(12) United States Patent
Shami et al.

(10) Patent No.: US 9,005,656 B2
(45) Date of Patent: Apr. 14, 2015

(54) ACTIVATED NITRIC OXIDE DONORS AND METHODS OF MAKING AND USING THEREOF

(75) Inventors: Paul J. Shami, Sandy, UT (US); Ken M. Kosak, West Valley City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 875 days.

(21) Appl. No.: 12/921,227

(22) PCT Filed: Mar. 5, 2009

(86) PCT No.: PCT/US2009/036100
§ 371 (c)(1),
(2), (4) Date: Apr. 14, 2011

(87) PCT Pub. No.: WO2009/114368
PCT Pub. Date: Sep. 17, 2009

(65) Prior Publication Data
US 2011/0182978 A1  Jul. 28, 2011

Related U.S. Application Data

(60) Provisional application No. 61/034,617, filed on Mar. 7, 2008.

(51) Int. Cl.
| | | |
|---|---|---|
| A61K 9/127 | (2006.01) | |
| A61K 31/56 | (2006.01) | |
| A61K 31/655 | (2006.01) | |
| A61K 9/107 | (2006.01) | |

(52) U.S. Cl.
CPC ............. *A61K 31/655* (2013.01); *A61K 9/1075* (2013.01); *A61K 9/127* (2013.01)

(58) Field of Classification Search
CPC ............................ A61K 31/00; A61K 9/1075
USPC .......................................... 514/9.7, 171, 150
See application file for complete search history.

(56) References Cited

U.S. PATENT DOCUMENTS

| | | | |
|---|---|---|---|
| 4,535,154 A | 8/1985 | Keefer et al. | |
| 4,954,526 A | 9/1990 | Keefer et al. | |
| 4,986,210 A | 1/1991 | Hollstein et al. | |
| 5,039,705 A | 8/1991 | Keefer et al. | |
| 5,155,137 A | 10/1992 | Keefer et al. | |
| 5,185,376 A | 2/1993 | Keefer et al. | |
| 5,208,233 A | 5/1993 | Keefer et al. | |
| 5,212,204 A | 5/1993 | Keefer et al. | |
| 5,250,550 A | 10/1993 | Keefer et al. | |
| 5,366,997 A | 11/1994 | Keefer et al. | |
| 5,389,675 A | 2/1995 | Christodoulou et al. | |
| 5,405,919 A | 4/1995 | Keefer et al. | |
| 5,525,357 A | 6/1996 | Keefer et al. | |
| 5,632,981 A | 5/1997 | Saavedra et al. | |
| 5,650,447 A | 7/1997 | Keefer et al. | |
| 5,676,963 A | 10/1997 | Keefer et al. | |
| 5,683,668 A | 11/1997 | Hrabie et al. | |
| 5,700,830 A | 12/1997 | Korthuis et al. | |
| 5,718,892 A | 2/1998 | Keefer et al. | |
| 5,721,365 A | 2/1998 | Keefer et al. | |
| 5,731,305 A | 3/1998 | Keefer et al. | |
| 5,814,656 A | 9/1998 | Saavedra et al. | |
| 5,814,666 A | 9/1998 | Green et al. | |
| 5,910,316 A | 6/1999 | Keefer et al. | |
| 6,057,367 A | 5/2000 | Stamler et al. | |
| 6,110,453 A | 8/2000 | Keefer et al. | |
| 6,200,558 B1 | 3/2001 | Saavedra et al. | |
| 6,265,420 B1 | 7/2001 | Lai | |
| 6,511,991 B2 | 1/2003 | Hrabie et al. | |
| 6,887,485 B2 | 5/2005 | Keefer et al. | |
| 2002/0119115 A1 | 8/2002 | Keefer et al. | |
| 2003/0147845 A1 | 8/2003 | Saavedra et al. | |
| 2005/0171066 A1 | 8/2005 | Shami | |

FOREIGN PATENT DOCUMENTS

| | | |
|---|---|---|
| EP | 1439187 | 7/2004 |
| WO | 9320806 | 10/1993 |
| WO | 9615781 | 5/1996 |
| WO | 9640055 | 12/1996 |
| WO | 9813358 | 4/1998 |
| WO | 9908112 | 2/1999 |
| WO | 0192215 | 12/2001 |

OTHER PUBLICATIONS

Pearce et al. Free Radic Biol Med. Jan. 1, 2008; 44(1), 73-81.*
Ren. et al. J. Cell. Physiology 197:426-434 (2003).*

(Continued)

*Primary Examiner* — Yong Chu
*Assistant Examiner* — Ana Z Muresan
(74) *Attorney, Agent, or Firm* — Gardner Groff Greenwald & Villanueva, PC

(57) ABSTRACT

Described herein are compositions useful in anticancer treatment and prevention. The compositions are composed of (a) an $O^2$-aryl substituted diazeniumdiolate and (b) an amphiphile, wherein the amount of amphiphile is sufficient to produce a liposome or micelle. The compositions described herein provide numerous advantages such as increased solubility and stability of the $O^2$-aryl substituted diazeniumdiolate in vivo. The compositions also do not induce hypotension. Methods for using the compositions in anticancer treatment and prevention are also described herein.

5 Claims, 6 Drawing Sheets

(56) References Cited

OTHER PUBLICATIONS

International Search Report and Combination Written Opinion in re PCT/US2009/036100, mailed Sep. 29, 2009.
Chrisey et al. (1996) "Covalent Attachment of Synthetic DNA to Self-Assembled Movolayer Films," Nucleic Acids Research, vol. 24, No. 15, 3031-3039.
Iwamoto et al., (1999) "Different cell cycle mechanisms between UV-induced and X-ray-induced apoptosis in WiDr colorectal carcinoma cells," Apoptosis 4:59-66.
Shami et al., (2006) "Antitumor Activity of JS-K [O2-(2,4-Dinitrophenyl) 1-[(4-Ethoxycarbonyl)piperazin-1-yl]diazen-1-ium-1,2-diolate] and Related O2-Aryl Diazeniumdiolates in Vitro and in Vivo," J. Med. Chem. 49:4356-4366.
Shami et al., (Apr. 2003) JS-K, a Glutathione/Glutathione S-Transferase-activated Nitric Oxide Donor of the Diazeniumdiolate Class with Potent Antineoplastic Activity1, Molecular Cancer Therapeutics, 2:409-417.
Anderson, M.E. (1998) Chem. Biol. Interact. 111-112:1-14.
Armstrong et al., (1994) Adv. Enzymol. Relat. Areas Mol. Biol. 69:1-44.
Armstrong et al., (1997) Chem. Res. Toxicol. 10:2-18.
Bico et al. (1994) Biochem. Mol. Biol. Int. 33:837-892.
Brunger et al., "Chrystallographic refinement by simulated annealing: Methods and Applications," Methods Enzymol. 277:243.269.
Cameron et al. (1995) Structure 3:717-727.
Cokic et al., (2003) Hydroxyurea induces fetal hemoglobin by the nitric oxide-dependent activation of soluble guanylyl cyclase, J. Clin. Invest. 111:231-239.
Dirr et al. (1994) Eur. J. Biochem. 220:645-661.
Engh et al. (1991) Acta Crystallogr. 47:392-400.
Habig (1974) Journal of Biochemistry, 249:7130-7139.
Hayes et al. (1995) Crit. Rev. Biochem. Mol. Biol. 30:445-600.
Ji et al. (1993) Biochemistry 32:12949-12954.
Jia et al. (1993) J. Pharmacol Exp Ther. 267:371-378.
Jones et al. (1997) "Electron-density map interpretation," Methods Enzymol. 277:173-208.
Keefer et al. (1996) Methods Enzymol. 268:281-293.
Magrinat et al. (1992) Blood 80:1880-1884.
Mancini et al. (1998) Tetrahedron Letters 39:1611-1614.
Martin et al. (1985) Blockade of endothelium-dependent and glyceryl trinitrate-induced relaxation of rabbit aorta by certain ferrous hemoproteins, J. Pharmacol Exp Ther 233:679-685.
Monga et al. (2002) Leukemia 16(4) 520-526.
Monks et al. (1991) "Feasibility of a high-flux anticancer drug screen using a diverse panel of cultured human tumor cell lines," J Natl Cancer Inst 83:757-766.
Ferrandina et al. (1997) "GGT activity in epithelial ovarian cancer," Annals of Oncology 8:343-350.
Moscow et al. (Sep. 1, 1988) "Isolation of the Human Anionic Glutathione S-Transferase cDNA and the Relation of Its Gene Expression to Estrogen-Receptor Content in Primary Breast Cancer," Proceedings of the National Academy of Sciences of the United States of America, 85:17, 6518-6522.
Shami et al., (1995) "Nitric Oxide Modulation of the Growth and Differentiation of Freshly Isolated Acute Non-Lymphocytic Leukemia cells," Leukemia Research, vol. 19, No. 8, 527-533.
Wilce et al. (1994) "Structure and function of glutathione S-transferases," Biochemica et Biophysica Acta 1205:1-18.
Sinning et al., (1993) "Structure Determination and Refinement of Human Alpha Class Glutathione Transferase A1-1, and a Comparison with the Mu and Pi Class Enzymes," J. Mol. Biol. 232, 192-212.
Shami et al. (1998) "Schedule and concentration-dependent induction of apoptosis in leukemia cells by nitric oxide," Leukemia 12, 1451-1466.
Saavedra et al. (1999) Piperazine as a Linker for Incorporating the Nitric Oxide-Releasing Diazeniumdiolate Group into Other Biomedically Relevant Functional Molecules, J. Org. Chem. 64, 5124-5131.
Saavedra et al. (2001) "The secondary amine/nitric oxide complex ion R(2)N[N(O)NO](-) as nucleophile and leaving group in S9N)Ar reactions," J. Org. Chem. 4, 66(9):3090-8.
Reference: Remington's pharmaceutical sciences: a treatise on the theory and practice of pharmaceutical sciences, with essential information about pharmaceutical and medical agents. Editorial board members: Arthur Osol et al.; Section editors: John T. Anderson et al.; Managing Editor: John E. Hoover. By Remington, Joseph P. Easton, Pa: Mack Publishing Co., 1975 15th ed.
Prade et al. (1997) "Structures of class pi glutathlone S-transferase from human placenta in complex with substrate, transition-state analogue and inhibitor," Research Article, 1287-1295.
Powell, 1977) "Restart Procedures for the Conjugate Gradient Method," Mathematical Programming 12, 241-254.
Nicoletti et al. (1991) "A rapid and simple method for measuring thymocyte apoptosis by propidium iodide staining and flow cytometry," Journal of Immunological Methods 139, 271-279.
Cui (1994) "Activated Murine Macrophages Induce Apoptosis in Tumor Cells through Nitric Oxide-dependent or -independent Mechanisms," Cancer Research 54, 2462-2467.
Japanese Office Action for application No. 2010549867 dated Aug. 20, 2013.
Kwon et al, "Enhanced tumor accumulation and prolonged circulation times of micelle-forming poly (ethylene oxide-aspartate) block copolymer-adriamycin conjugates", Journal of Controlled Release, 29, 1994, 17-23.
Patel, "Poloxamers: A pharmaceutical excipients with therapeutic behaviors", International Jounral of PharmTech Research, Apr.-Jun. 2009.
Kataoka, "Block copolymer micelles as vehicles for drug delivery", Journal of Controlled Release, 1993, 119-132.

* cited by examiner

JS-K

JXC-2-40

JXC-2-56

JS-36-25

ACTIVATED NITRIC OXIDE DONORS AND METHODS OF MAKING AND USING THEREOF

CROSS REFERENCE TO RELATED APPLICATIONS

This application claims priority upon U.S. provisional application Ser. No. 61/034,617, filed Mar. 7, 2008. This application is hereby incorporated by reference in its entirety for all of its teachings.

ACKNOWLEDGEMENTS

The research leading to this invention was funded in part by the National Institutes of Health grant number RO1 CA129611. The U.S. Government has certain rights in this invention.

BACKGROUND

Cancer, the uncontrolled growth of malignant cells, is a major health problem of the modern medical era and ranks second only to heart disease as a cause of death in the United States. Acute Myelogenous Leukemia ("AML") is the most common acute leukemia in adults (Greer, J. P., et al. (2004) Wintrobe's Clinical Hematology, Baltimore pp. 2098-2142). Most patients who contract this disease succumb to it. Since the early seventies, the mainstay of therapy has been cytosine arabinoside (Ara-C) and anthracyclines (Greer, J. P., et al. (2004) Wintrobe's Clinical Hematology, Baltimore pp. 2098-2142). With the notable exception of all-trans retinoic acid for the treatment of acute promyelocytic leukemia, no new agent has had a major impact on disease outcome.

Stem cell transplantation has its limitations due to patients' age and availability of suitable donors. Furthermore, recent trials suggest that high dose therapy with stem cell rescue may not offer a survival advantage over standard dose chemotherapy (Cassileth, P. A., et al. (1998) New England Journal of Medicine 339(23): 1649-1656). Consequently, the need for new agents with new mechanisms of action for the treatment of AML and other types of cancer is evident.

Nitric oxide (NO) is a unique cytotoxic agent because of its multiple intracellular targets. As such, it constitutes an extremely potent antineoplastic agent. The main problem with NO has been the induction of hypotension by NO-generating compounds because of NO's pleotropic effects. It is known that NO is a major biologic effector molecule with functions in the vascular, immunologic and neurologic systems (Moncada, S., et al. (1991) Pharmacological Reviews 43:109-142). NO is produced in vivo by the nitric oxide synthases (NOS) (Moncada, S., et al. (1991) Pharmacological Reviews 43:109-142). For example, NO inhibits the growth of normal and malignant cells (Nathan, C. (1992) FASEB Journal 6:3051-3064). Additionally, NO inhibits growth and induces differentiation in AML cells (Magrinat, G., et al. (1992) Blood 80:1980-1986; Shami, P. J., et al. (1995) Leukemia Research 19; 527-533; Shami, P. J., et al. (1998) Leukemia 12: 1461-1466). A problem with widespread in vivo use of NO is its non-specific action on non-cancerous cells including its effects on vascular tissue resulting in hypotension.

SUMMARY

Described herein are compositions useful in anticancer treatment and prevention. The compositions are composed of (a) an $O^2$-aryl substituted diazeniumdiolate and (b) an amphiphile, wherein the amount of amphiphile is sufficient to produce a liposome or micelle. The compositions described herein provide numerous advantages such as increased solubility and stability of the $O^2$-aryl substituted diazeniumdiolate in vivo. The compositions also do not induce hypotension. Methods for using the compositions in anticancer treatment and prevention are also described herein. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
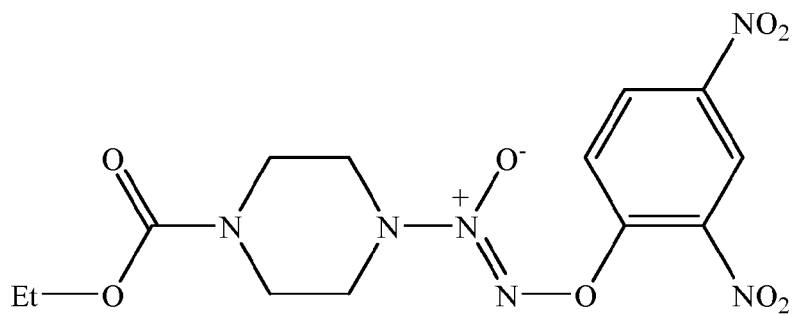
FIG. 1 shows the structures of several $O^2$-aryl substituted diazeniumdiolates useful herein.
Figure 1:
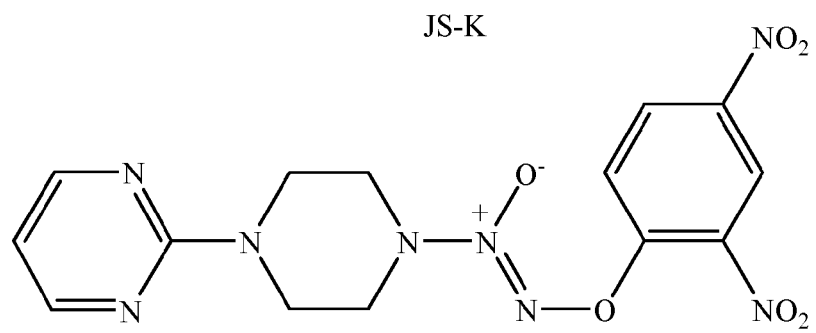
Figure 1:
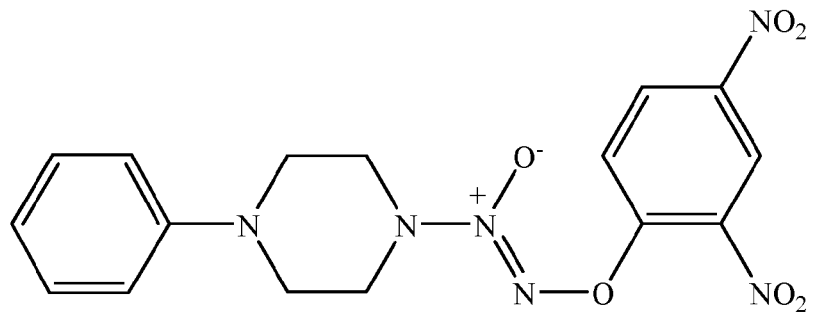
Figure 1:
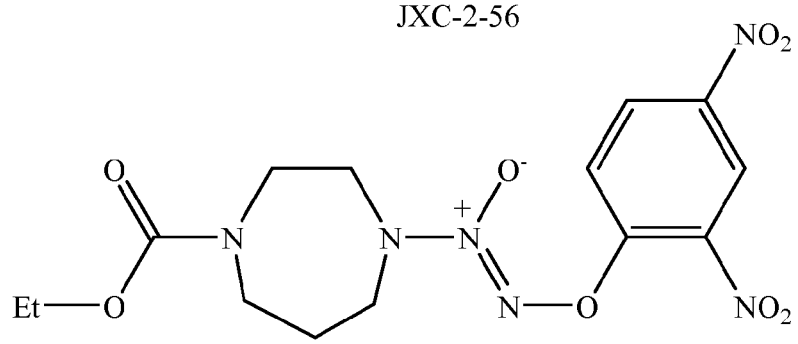

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound. A weight percent of a component, unless specifically stated to the contrary, is based on the total weight of the formulation or composition in which the component is included.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, halo, hydroxy, alkylthio, arylthio, alkoxy, aryloxy, amino, mono- or di-substituted amino, ammonio or substituted ammonio, nitroso, cyano, sulfonato, mercapto, nitro, oxo, alkyl, alkenyl, cycloalkyl, benzyl, phenyl, substituted benzyl, substituted phenyl, benzylcarbonyl, phenylcarbonyl, saccharides, substituted benzylcarbonyl, substituted phenylcarbonyl and phosphorus derivatives. The aryl group can include two or more fused rings, where at least one of the rings is an aromatic ring. Examples include naphthalene, anthracene, and other fused aromatic compounds.

The term "reduce" refers to lowering the rate of cancer cell growth or tumor growth. For example, the cancer cell growth rate can be reduced by 5%, 10%, 20%, 30%, 40%, 50%, 60%, 70%, 80%, 90%, or 99% when compared to a positive control.

The term "prevent" refers to zero cancer cell growth rate or tumor growth when compared to a positive control.

The term "hypotension" refers to an abnormal condition in which the blood pressure of a subject is low enough to cause symptoms or interfere with well-being. For example, a subject having a blood pressure lower than 90/60 can be experiencing hypotension.

The term "micelle" refers an aggregate of amphiphilic molecules dispersed in a liquid colloid. A typical micelle in aqueous solution forms an aggregate with the hydrophilic "head" regions in contact with surrounding medium, sequestering the hydrophobic tail regions in the micelle center. The shape and size of a micelle is a function of the molecular geometry of the amphiphiles and solution conditions such as amphiphile concentration, temperature, pH, and ionic strength. The $O^2$-aryl substituted diazeniumdiolate is for the most part incorporated within the hydrophobic portion of the micelle.

The term "liposome" refers to a bilayered system produced by an amphiphile. A aqueous core is present in the liposome as a result of the hydrophobic tails of the amphiphile lining up to produce the bilayer.

Variables such as A, X, Y, $R^1$-$R^4$, a, b, m, n, o, and p used throughout the application are the same variables as previously defined unless stated to the contrary.

I. Compositions and Preparation Thereof

Described herein are pharmaceutical compositions useful for anticancer treatment. The compositions are useful in delivering NO in vivo to a subject. NO is a potent cytotoxin that contributes to the host's immune defense against microbial and tumor cell growth (Moncada, S., et al. (1991) Pharmacological Reviews 43:109-142; (Nathan, C. (1992) FASEB Journal 6:3051-3064). Indeed, NO is potently cytotoxic to tumor cells in vitro (Rangei-Yagui, C. O., et al. (2005) J. Pharm. Pharma. Sci. 8(2):147-63). NO inhibits growth and induces differentiation and apoptosis in AML cells (Magrinal, G., et al. (1992) Blood 80:1980-1986; Shami, P. J., et al. (1995) Leukemia Research 19; 527-533; Shami, P. J., et al. (1998) Leukemia 12: 1461-1466). NO has multiple intracellular targets that could inhibit cellular growth and thus, with targeted delivery, is a very attractive molecule to use as an antineoplastic agent (Henry, Y., et al. (1993) FASEB Journal 7:1124-1134); 17-28). These mechanisms and targets include, protein tyrosine nitrosation (by generating peroxynitrite in the presence of superoxide), protein thiol nitrosylation, ADP ribosylation, inhibition of mitochondrial respiration, inhibition of ribonucleotide reductase, protein glutathionylation, and induction of DNA strand breaks (Henry, Y., et al. (1993) FASEB Journal 7:1124-1134); 17-28).

Although NO has numerous advantages and applications in cancer treatment and therapy, it is a potent vasodilator and induces hypotension by activating the soluble guanylate cyclase (sGC)/cGMP signal transduction pathway in the vasculature (Moncada, S., et al. (1991) Pharmacological Reviews 43:109-142; (Nathan, C. (1992) FASEB Journal 6:3051-3064). This property makes the in vivo administration of drugs that spontaneously generate NO in solution (such as sodium nitroprusside) for antineoplastic purposes not feasible. The compositions described herein address these limitations.

The compositions described herein are composed of $O^2$-aryl substituted diazeniumdiolates in liposomes or micelles that can be readily administered to a subject for the treatment of cancer. The compositions and methods are described in detail below.

a. $O^2$-Aryl Substituted Diazeniumdiolates

Diazeniumdiolates are compounds having an $N_2O_2$ functional group. The $O^2$-aryl substituted diazeniumdiolates disclosed in U.S. Pat. No. 6,610,660 and methods for preparing the same can be used herein, the teachings of which are incorporated by reference. In one aspect, the $O^2$-aryl substituted diazeniumdiolate has the formula I

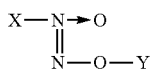

Figure 10:
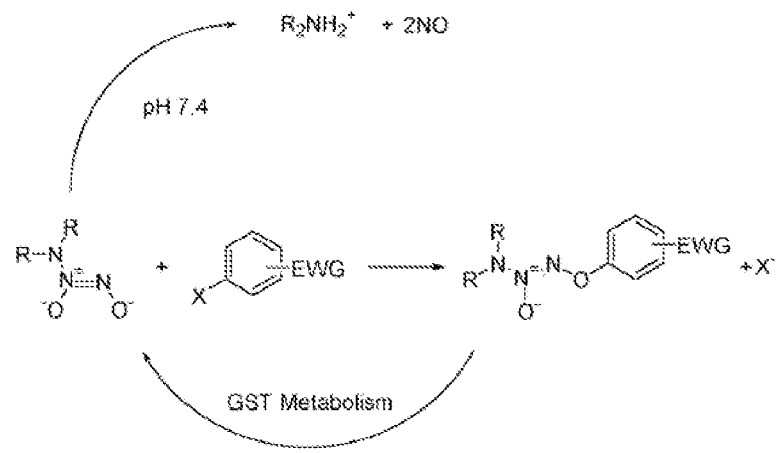
FIG. 10 illustrates a scheme of GST-activated NO donor design.
Figure 11:
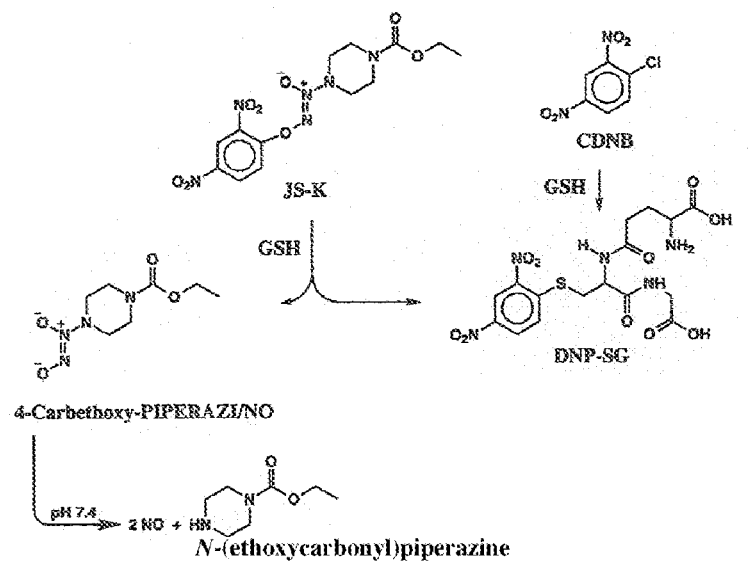
FIG. 11 illustrates JS-K structure and reaction mechanism in vivo.

I wherein X includes an organic moiety and Y includes an aryl group, wherein an atom of the ring of the aryl group is bonded to the $O^2$-oxygen, or the pharmaceutically acceptable salt or ester thereof. When Y is cleaved from the compound of formula I, NO is released spontaneously. Not wishing to be bound by theory, Glutathione-S-Transferases (GST) can cleave Y and generate NO in vivo in a subject (see FIG. 10 for a general mechanism and FIG. 11 for a specific mechanism using JSK). Glutathione-S-Transferases are overexpressed in many forms of leukemia and solid tumors. Thus, the delivery of compounds having the formula I to cancer cells followed by subsequent cleavage of the compound to produce NO in vivo is an effective way to treat cancer. The compositions described herein provide an effective way to deliver diazeniumdiolates such as those in formula I to cancer cells.

In one aspect, X in formula I can be a substituted or unsubstituted alkyl group, cycloalkyl group, a heterocycloalkyl group, or an aryl group. In another aspect, X is a heterocycloalkyl group having at least one nitrogen atom incorporated within the ring. Examples of such heterocycloalkyl groups include, but are not limited to, a group having the formula II, III, or IV

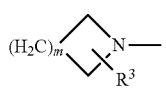

II

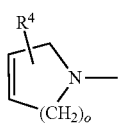

III

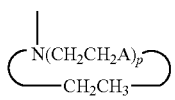

IV wherein A is N, O, or S, m is 1-12, o is 1 or 2, p is 1-5, $R^3$ is hydrogen, an alkyl group (e.g., $C_1$-$C_8$ straight chain or $C_3$-$C_8$ branched chain alkyl group), a cycloalkyl group (e.g., $C_3$-$C_8$), an aryl group, a carboxylato group, and $R^4$ is hydrogen, or an alkyl group (e.g., $C_1$-$C_6$ straight chain alkyl group or a $C_3$-$C_6$ branched chain).

In other aspects, X is a group having the formula V

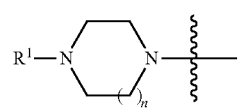

V wherein n is one or 2 and $R^1$ is a substituted or unsubstituted aryl group, a substituted or unsubstituted heteroaryl group, or an ester having the formula —C(O)O$R^2$ or a ketone having the formula —C(O)$R^2$, wherein $R^2$ comprises an alkyl group or an aryl group. For example, referring to formula V, n is one and $R^1$ can have the formula —C(O)O$R^2$, wherein $R^2$ is a $C_1$-$C_5$ alkyl group. In another aspect, n in formula V is one and $R^1$ has the formula —C(O)OEt.

Y in formula I includes an aryl group, wherein an atom of the ring of the aryl group is bonded to the $O^2$-oxygen. Examples of aryl groups useful herein include, but are not limited to, an acridine, an anthracene, a benzene, a benzofuran, a benzothiophene, a benzoxazole, a benzopyrazole, a benzothiazole, a carbazole, a chlorophyll, a cinnoline, a furan, an imidazole, an indole, an isobenzofuran, an isoindole, an isoxazole, an isothiazole, an isoquinoline, a naphthalene, an oxazole, a phenanthrene, a phenanthridine, a phenothiazine, a phenoxazine, a phthalimide, a phthalazine, a phthalocyanine, a porphin, a pteridine, a purine, a pyrazine, a pyrazole, a pyridazine, a pyridine, a pyrimidine, a pyrrocoline, a pyrrole, a quinolizinium ion, a quinoline, a quinoxaline, a quinazoline, a sydnone, a tetrazole, a thiazole, a thiophene, a thyroxine, a triazine, or a triazole.

In another aspect, Y can be identical to or structurally analogous to molecules, or substituents thereof, normally found in living organisms. These biologically relevant groups can be a vitamin or a derivative thereof, a hormone or a derivative thereof, a pyrimidine or a derivative thereof, a ribosylpyrimidine or a derivative thereof, a purine or a derivative thereof, or a ribosylpurine or a derivative thereof. In other aspects, Y can be a nucleotide, nucleoside, and nucleic acid; peptides, including peptide hormones, non-peptide hormones, vitamins and other enzyme cofactors such as porphyrins, and others. Examples of biologically relevant aryl groups are thyroxine, NAD (or NADH), chlorophyll, hypoxanthine, uridine, and vitamin $K_5$. In these aspects, the above-identified compounds possess an aryl group.

The aryl group present in Y can be substituted with a variety of groups. In one aspect, Y has at least at least one nitro group. In another aspect, Y is a phenyl group having at least one nitro group or two nitro groups. In one aspect, Y has the formula VI

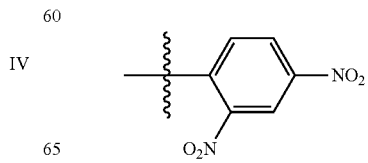

VI

In another aspect, the O²-aryl substituted diazeniumdiolate is O²-(2,4-dinitrophenyl) 1-[(4-ethoxycarbonyl)piperazin-1-yl]diazen-1-ium-1,2-diolate (JS-K), O²-(2,4-dinitrophenyl) 1-[4-phenylpiperazin-1-yl]diazen-1-ium-1,2-diolate (JXC-2-40), O²-(2,4-dinitrophenyl) 1-[4-pyrimidin-2-yl)piperazin-1-yl]diazen-1-ium-1,2-diolate (JXC-2-56), or O²-(2,4-dinitrophenyl) 1-[(4-ethoxycarbonyl)-2,4-diazacycloheptan-1-yl]diazen-1-ium-1,2-diolate (JS-36-25). The structures of these compounds are provided in FIG. 1.

Any of the O²-aryl substituted diazeniumdiolates described herein can be the pharmaceutically acceptable salt or ester thereof. Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of compounds of structural formula I to base used are chosen to provide the ratio desired for any particular salts. For preparing, for example, the ammonium salts of the free acid starting material, the starting material can be treated with approximately one equivalent of pharmaceutically acceptable base to yield a neutral salt.

Ester derivatives are typically prepared as precursors to the acid form of the compounds—as illustrated in the examples below—and accordingly can serve as prodrugs. Generally, these derivatives will be lower alkyl esters such as methyl, ethyl, and the like. Amide derivatives —(CO)NH$_2$, —(CO)NHR and —(CO)NR$_2$, where R is an alkyl group defined above, can be prepared by reaction of the carboxylic acid-containing compound with ammonia or a substituted amine.

b. Amphiphile

Amphiphiles useful herein are compounds possessing hydrophilic and lipophilic groups capable of forming micelles or liposomes. The amphiphiles should be biocompatible such that they possess minimal toxicity. Amphiphiles useful herein for preparing liposomes and micelles include homopolymers, copolymers, block-copolymers produced from biocompatible and biodegradable materials. Examples of such polymers include, but are not limited to, poly(amino acids); polylactides; poly(ethyleneimines); poly(dimethylaminoethylmethacrylates), copolymers of polyethyelene glycol and hydroxyalkyl acrylates and acrylamides (e.g., N-(2-hydroxypropyl)methacrylamide), PEG-β-poly(α-amino acids), poly(L-lactic acid)-poly(ethylene glycol) block copolymers, or poly(L-histidine)-poly(ethylene glycol) block copolymers.

In one aspect, the amphiphile is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

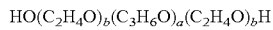

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, those in Table 1.

TABLE 1

| Copolymer | MW | Average number of EO units | Average number of PO units | CMC (M) |
|---|---|---|---|---|
| F68 | 8,400 | 152.73 | 28.97 | $4.8 \times 10^{-4}$ |
| P103 | 4,950 | 33.75 | 59.74 | $6.1 \times 10^{-6}$ |
| P105 | 6,500 | 73.86 | 56.03 | $6.2 \times 10^{-6}$ |
| P123 | 5,750 | 39.2 | 69.4 | $4.4 \times 10^{-6}$ |
| F127 | 12,600 | 200.45 | 65.17 | $2.8 \times 10^{-6}$ |
| L121 | 4,400 | 10.00 | 68.28 | $1.1 \times 10^{-6}$ |

In other aspects, the amphiphile can be a lipid such as phospholipids, which are useful in preparing liposomes. Examples include phosphatidylethanolamine and phosphatidylcholine. In other aspects, the amphiphile includes cholesterol, a glycolipid, a fatty acid, bile acid, or a saponin.

c. Preparation of Compositions

The compositions described herein can be readily prepared by mixing the O²-aryl substituted diazeniumdiolate and amphiphile in the appropriate concentrations in a solvent to produce the micelle or liposome. In certain aspects, the O²-aryl substituted diazeniumdiolate and amphiphile are mixed in water followed by heating to produce micelles. The amount of O²-aryl substituted diazeniumdiolate and amphiphile can vary. In one aspect, the amount of amphiphile should be sufficient such that the critical micelle concentration (CMC) is reached. The critical micelle concentration (CMC) is defined as the concentration of surfactants above which micelles are spontaneously formed. Table 1 provides the CMC of poloxamers useful herein as amphiphiles. In certain aspects, the concentration of amphiphile used can be several fold higher than the CMC of the amphiphile. It is contemplated that additional bioactive agents can be incorporated into the micelle or liposome in addition to the O²-aryl substituted diazeniumdiolate. For example, other anticancer agents described below can be used herein in this aspect.

In certain aspects, additives can be used to increase the stability of the compositions described herein. In one aspect, additives such as albumin when added to the amphiphile and O²-aryl substituted diazeniumdiolate can stabilize the resulting micelle or liposome. For example, the addition of 1% human serum albumin to 1 mM of JS-K dissolved in 2% P123 Pluronic® resulted in the formation of micelles that are significantly more stable.

The compositions described herein are very stable. In other words, the O²-aryl substituted diazeniumdiolate is protected from stringent physiological conditions such as exposure to serum and peptides like GSH. Additionally, the compositions are easy to handle and can withstand purification steps such as filtration without the O²-aryl substituted diazeniumdiolate leaching from the composition. Finally, the compositions are soluble in water. In general, O²-aryl substituted diazeniumdiolates are water insoluble. Thus, when the O²-aryl substituted diazeniumdiolate is incorporated in a micelle or liposome, it is much easier to administer the O²-aryl substituted diazeniumdiolate to the subject.

d. Pharmaceutical Compositions

In one aspect, any of the compositions described herein can be combined with at least one pharmaceutically-acceptable carrier to produce a pharmaceutical composition. The pharmaceutical compositions can be prepared using techniques known in the art. In one aspect, the composition is prepared by admixing the composition with a pharmaceutically-acceptable carrier. The term "admixing" is defined as mixing the two components together so that there is no chemical reaction or physical interaction. The term "admixing" also includes the chemical reaction or physical interaction between the compound having the formula I and the pharmaceutically-acceptable carrier.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be parenterally, orally, subcutaneously, intralesionally, intraperitoneally, intraveneously, or intramuscularly.

Preparations for administration include sterile aqueous or non-aqueous solutions, suspensions, and emulsions. Examples of non-aqueous carriers include alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

It will be appreciated that the actual preferred amounts of active compound in a specified case will vary according to the specific compound being utilized, the particular compositions formulated, the mode of application, and the particular situs and mammal being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing (1999).

II. Methods of Use

The compositions described herein are effective anticancer agents. Tumor cell resistance to chemotherapeutic agents represents a major problem in clinical oncology. In order to inhibit cell growth, induce cell differentiation, induce apoptosis, inhibit MDR phenotype, inhibit metastasis, inhibit angiogenesis or otherwise reverse or reduce the malignant phenotype of tumor cells using the methods and compositions of the present invention, a "target" cell is contacted with one or more compositions described herein. In certain aspects, the composition composed of the $O^2$-aryl diazeniumdiolate compound and at least one other agent can be administered. The compositions described herein can improve the efficacy of chemo- and radiotherapy. One approach involves using the compositions described herein in combination with chemo- or radiotherapeutic intervention. This treatment option may offer a combinatorial therapeutic effect along with the DNA damaging agent. Different cancer therapeutic agents and methods of treatment utilizing such agents are well-known in the art.

In one aspect, the additional agent can be an anticancer agent. These compositions can be provided in a combined amount effective to kill or inhibit proliferation of the cell. This process may involve contacting the cells with the compositions and the agent(s) or factor(s) at the same time. This may be achieved by contacting the cell with a single composition or pharmacological formulation that includes both agents (e.g., $O^2$-aryl diazeniumdiolate and chemotherapeutic agent), or by contacting the cell with two distinct compositions or formulations simultaneously, wherein one composition includes the $O^2$-aryl diazeniumdiolate composition described herein and the other includes the agent.

Alternatively, any of the $O^2$-aryl diazeniumdiolate composition treatments may precede or follow the other agent treatment by intervals ranging from minutes to weeks. In aspects where the other agent and any of the $O^2$-aryl diazeniumdiolate compositions described herein are applied separately to the cell, a significant period of time should not expire between the time of each delivery, such that the agent and $O^2$-aryl diazeniumdiolate compound would still be able to exert an advantageously combined (e.g., synergistic) effect on the cell. In one aspect, the cell can be contacted with both modalities within about 12-24 h, or from about 6-12 h of each other, with a delay time of up to about 12 h. In some situations, it may be desirable to extend the duration of treatment with just the therapeutic agent, for example, where several days (2, 3, 4, 5, 6 or 7) to several weeks (1, 2, 3, 4, 5, 6, 7 or 8) lapse between the respective administrations.

Examples of anticancer agent include, but are not limited to, platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

The methods described herein are applicable for treating a variety of different types of cancers. In one aspect, the cancer includes prostate, leukemia (e.g., acute myelogenous leukemia, acute promyelocytic, acute lymphoblastic leukemia, chronic myelogenous leukemia, chronic lymphocytic leukemia, hairy cell leukemia, plasma cell leukemia), myeloproliferative disorders (e.g., essential thrombocytosis, polythemia vera, primary myelofibrosis), myelodysplastic syndromes, lymphoma (Hodgkin and non-Hodgkin), testicular, head and neck, esophagus, stomach, liver, small intestine, gall bladder, rectum, anus, sarcoma, uterus, cervix, bladder, bone, renal, melanoma, colon, ovarian, lung, central nervous system, multiple myeloma, skin, or breast cancer. One of the many advantages of the compositions described herein is that while effective in anticancer treatment, the compositions do not induce hypotension. As discussed above, a problem with widespread in vivo use of NO is its non-specific action on non-cancerous cells including its effects on vascular tissue resulting in hypotension. The compositions described avoid this problem, which makes them even more attractive in anticancer treatment and prevention.

In other aspects, the compositions described herein can be used as a purging agent. For example, stem cells can be collected from a patient afflicted with cancer (e.g., leukemia or multiple myeloma), and the stem cells can be treated with the compositions described herein to kill any residual malignant cells. This is also referred to herein as "purging" the graft. The treated stem cell can be subsequently used for a stem cell (bone marrow) transplant on the patient after high doses of chemotherapy/radiation.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Figure 2:
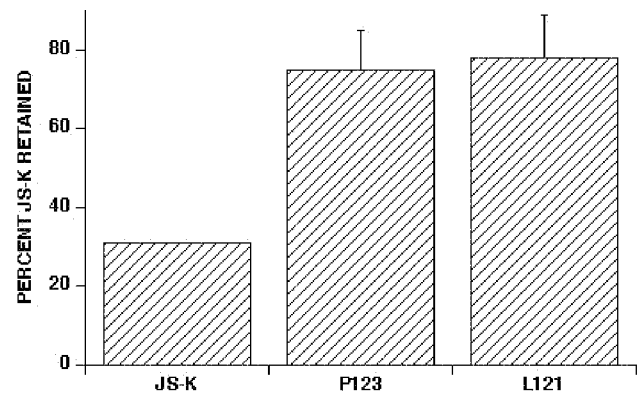
FIG. 2 is a bar graph comparing the dialysis of free JS-K vs. JS-K in Pluronic® micelles.

This example illustrates the extent of JS-K loading in micelles. JS-K was loaded in Pluronic® P123 and L121 polymers to form micelles. The proportion of JS-K to Pluronic® polymer in solution was 10% by weight. The JS-K micelle preparations were then dialyzed for 2 hours. A parallel experiment following the same procedures with free JS-K was set up as a control. After 2 hours of dialysis, JS-K levels were measured by HPLC to estimate the percent of JS-K retained. Percent retention of free JS-K was only 31% as compared to 75±10% and 78±11% for JS-K in Pluronic® P123 and L121 micelles, respectively, see FIG. 2. The results showed that JS-K in a micellar formulation is retained after dialysis, while free JS-K is mostly lost during dialysis.

Example 2

Figure 3:
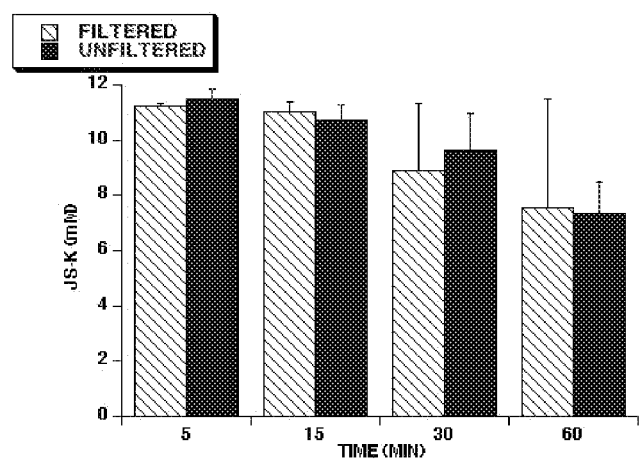
FIG. 3 is a bar graph showing the effect of filtration on JS-K stability in Pluronic® micelles.

This example illustrates the effect of filtration on Pluronic® micelles. JS-K was loaded in P123 micelles (the proportion of JS-K to Pluronic® polymer in solution was 1.57% by weight). Aliquots of the JS-K preparation were then filtered through a 0.2 µM membrane filter and kept at room temperature. At regular intervals 20 µL aliquots from the preparations were collected and JS-K levels were measured by HPLC. Parallel measurements were done on similar JS-K formulations in P123 Pluronic® micelles that had not been filtered. Measured JS-K levels went down with time. The results show there were no differences in JS-K concentrations between filtered and unfiltered micelles, suggesting that these micelles can be filtered without degradation, see FIG. 3.

Example 3

This example illustrates that Pluronic® micelles stabilize JS-K in the presence of GSH. In these experiments, free JS-K and JS-K formulated in Pluronic® P-123 micelles were incubated at a concentration of 10 mM with 4.0 mM GSH in PBS at pH 7.4 and room temperature. The proportion of JS-K to Pluronic® polymer in solution was 1.57% by weight. At regular intervals, JS-K levels were measured by HPLC. Under these conditions, free JS-K had a half-life of 6 minutes in the presence of GSH. JS-K in P-123 micelles in the presence of GSH under the same conditions had a half-life of 37 minutes. These results show that Pluronic® micelles substantially prolong the half-life (by 6 fold in the case of P-123) of JS-K under very stringent conditions of nucleophilic attack by free thiols represented by GSH.

Example 4

This example illustrates the stability of free JS-K vs. JS-K in Pluronic® micelles in serum. JS-K was loaded in L121 and P123 Pluronic® micelles. The proportion of JS-K to Pluronic® polymer in solution was 0.98% by weight. Pluronic® JS-K was then incubated at 37° C. with FBS in a total volume of 8 mL. The final concentration of JS-K was 100 µM. The final concentration of FBS was 90% v/v. The pH was 7.6. Controls were set-up under the same conditions using free JS-K at the same concentration. One mL aliquots were taken at regular intervals. After dichloromethane extraction, JS-K levels were measured by HPLC using the protocol outlined above. The experiment was done in duplicate and measurements were used to calculate the half-life of the different formulations of JS-K in serum.

Under these conditions, free JS-K had a half-life of 1.2 minutes. JS-K in L121 Pluronic® micelles had a half-life of 71 minutes, while JS-K in P123 micelles had a half-life of 91 minutes. These experiments reproduce more closely in vivo conditions than free GSH and show the ability of Pluronic® micelles to stabilize JS-K under very stringent conditions of exposure to proteins and macromolecules.

Example 5

This example measures the particle size of JS-K in Pluronic® micelles and the pH effect. Using dynamic light scattering with a Malvern 3000 Zetasizer (Malvern Instruments, Worstershire, UK), the particle size of Pluronic® P123 micelles with and without JS-K under different pH conditions was measured. Measurements were conducted on 4 separate samples in PBS in 3 mL volumes. In one set of experiments, P123 micelles we made (without JS-K) under different pH conditions ranging from 4.5 to 7.4. After equilibration at room temperature for 4 hours, particle size was measured. No aggregation was observed, indicating preservation of micelle integrity. Results in Table 2 show that pH does not affect size (and hence stability) of P123 Pluronic® micelles.

TABLE 2

Effect of pH on Particle size of Pluronic ® P123 micelles

| pH | Particle size (nm ± SD) |
|---|---|
| 4.5 | 18.23 ± 5.36 |
| 5.0 | 17.4 ± 5.14 |
| 7.4 | 19.03 ± 5.62 |

In another set of experiments, JS-K was loaded in P123 micelles at pH 7.4 and particle size was measured at different intervals. The proportion of JS-K to Pluronic® polymer in solution was 0.52% by weight. Results in Table 3 show that over the observation period, P123 micelles loaded with JS-K were stable.

TABLE 3

Effect of JS-K loading in Pluronic ® P123 micelles on particle size (pH 7.4)

| Time (min) | Particle size (nm ± SD) |
|---|---|
| 2 | 19.18 ± 5.64 |
| 15 | 19.55 ± 5.74 |
| 30 | 19.55 ± 5.74 |
| 45 | 19.75 ± 5.84 |

Again, no aggregation was observed, indicating preservation of the micelle integrity. Three conclusions can be drawn from these measurements. First, under these conditions, Pluronic® micelles are very stable over the observation period. Second, JS-K loading of the micelles did not affect particle size or micelle stability. Third, within the range studied, pH did not affect micelle stability.

Example 6

Figure 4:
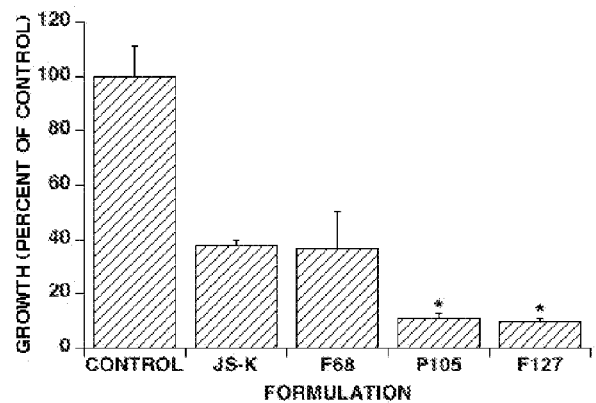
FIG. 4 is a bar graph showing the cytotoxicity of free JS-K vs JS-K in Pluronic® micelles.

The in vitro cytotoxicity of JS-K in Pluronic® micelles was studied in this example. JS-K was loaded in F68, P105, or F127 Pluronic® micelles as described above. The proportion of JS-K to Pluronic® polymer in solution was 4% by weight. Free JS-K or micellar JS-K was then added to HL-60 cells at a concentration of 0.5 µM. Similar control experiments were set-up with equivalent concentrations of each Pluronic® micelle without JS-K. After a 3 day incubation, cell growth was measured using the MTS assay. Free JS-K inhibited leukemia cell growth by 62% (FIG. 4). F68 micelles did not increase JS-K's cytotoxic effects, while JS-K formulated in P105 or F127 micelles inhibited cell growth by around 90% each (FIG. 4). Equivalent empty micelles at equal concentrations (0.08% w/v) had no significant effect on cell growth (not shown).

Figure 5:
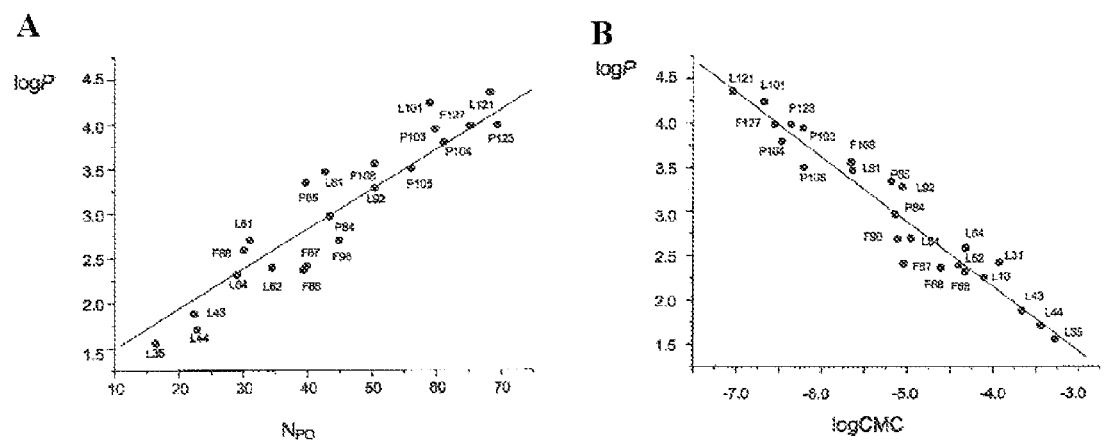
FIG. 5A and FIG. 5B show the characterization of Pluronic® micelles.

These results demonstrate that Pluronic® micelle formulations can increase the efficacy of JS-K. As expected, the Pluronic® polymers with the highest CMC and lowest partitioning coefficient (Table 1 and FIG. 5) did not improve the effectiveness of free JS-K. P105 and F127 which have CMC's and partitioning coefficients in the same range (Table 2, and FIG. 3) increased JS-K's cytotoxicity to approximately the same extent.

Figure 6:
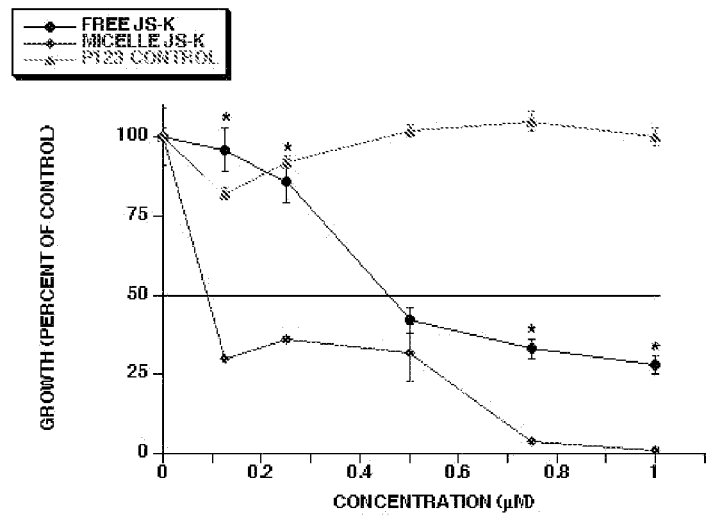
FIG. 6 is a bar graph showing the cytotoxicity of free JS-K vs JS-K in Pluronic® P123 micelles.

In other experiments, JS-K was loaded in Pluronic® P123 micelles and its in vitro cytotoxicity towards HL-60 cells was compared to free JS-K. The proportion of JS-K to Pluronic® polymer in solution was 1.97% by weight. The results showed that formulating JS-K in Pluronic® P123 micelles decreased its in vitro $IC_{50}$ from 0.45 to 0.09 µM, indicating a substantial increase in its cytotoxic activity (FIG. 6). These results are likely due to stabilization of JS-K in the micelles and increased intracellular accumulation of the drug.

Example 7

This example illustrates the effect of JS-K in Pluronic® micelles on systemic blood pressure. JS-K was loaded in Pluronic® P123 micelles and used in in vivo experiments to determine whether a Pluronic® micelle formulation of JS-K affects JS-K's effect on systemic blood pressure. The proportion of JS-K to Pluronic® polymer in solution was 1.53% by weight.

Figure 7:
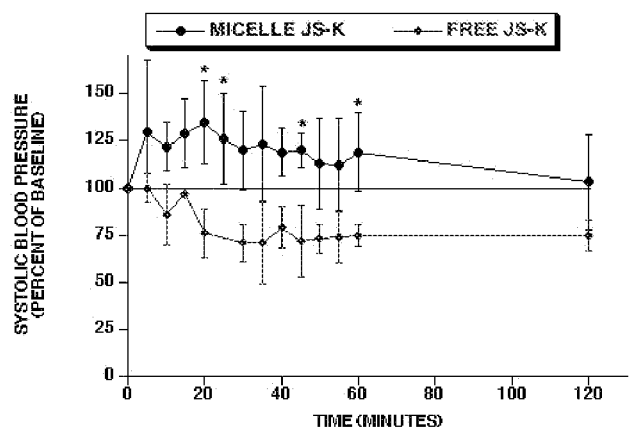
FIG. 7 is a graph showing JS-K in Pluronic® micelles and systemic blood pressure.

Awake, unanesthetized NOD/SCID and NOD/SCID IL2R$\gamma^{null}$ mice were used for these experiments. Mice were treated with escalating intravenous doses of JS-K in P123 micelles or free JS-K. Systolic blood pressure was measured using the tail cuff technique every 5 minutes for 1 hour and then at the 2 hours time point. Free JS-K at a dose of 5 µmol/kg led to a sustained drop in systolic blood pressure of around 20% of baseline while JS-K in P123 micelles at the same dose did not (FIG. 7).

The fact that JS-K in P123 micelles did not induce hypotension while free JS-K did so at equal doses shows indirect proof that a Pluronic® micelle formulation of JS-K stabilizes the drug in vivo in the bloodstream. Hypotension observed at higher doses is likely due to the dynamic equilibrium between free drug and JS-K in micelles.

Example 8

Figure 8:
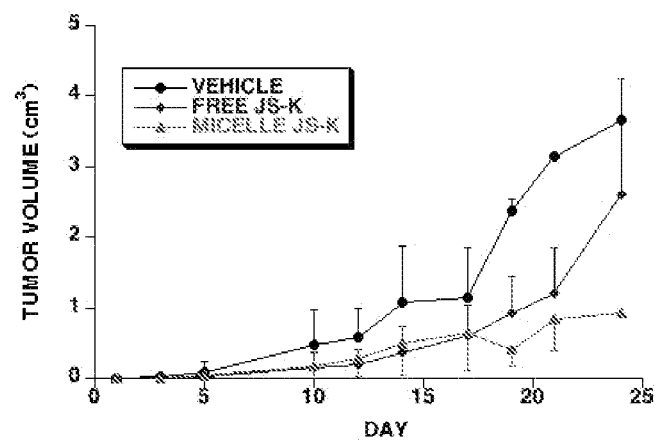
FIG. 8 is a graph showing JS-K in Pluronic® micelles on HL-60 cell growth in vivo.

This example illustrates the in vivo anti-leukemic activity of JS-K in Pluronic® micelles. NOD/SCID IL2R$\gamma^{null}$ mice were inoculated with 5×10$^6$ HL-60 cells in each flank. When tumors became palpable, treatment was started with 3 variables as follows: 1—controls injected with empty Pluronic® P123 micelles (4 mice); 2—mice injected with free JS-K (3 mice); and 3—mice injected with JS-K formulated in Pluronic® P123 micelles (3 mice). The proportion of JS-K to Pluronic® polymer in solution was 2.0% by weight. Injections were given 3 times per week intravenously. The dose of free and micelle-formulated JS-K was 4 µmol/kg. Micelle-formulated JS-K treatment led to a delay in tumor growth to a greater extent than free drug. A linear mixed model using SAS PROC MIXED was fit to the data in FIG. 8, using a random effect to account for correlation among measurements within the same animal. In this model, rate of tumor growth, as fit by a linear and quadratic effect of time, was found to be significantly higher (p=0.01 by F-test) among animals treated with free JS-K compared to animals treated with JS-K formulated in Pluronic® P123 micelles.

The results confirm the in vivo antineoplastic activity of JS-K and suggest increased anti-tumor efficacy of JS-K in a Pluronic® micelle formulation. This is very likely due to stabilization of the drug by the micelles and therefore increased drug delivery to tumors.

Example 9

Figure 9:
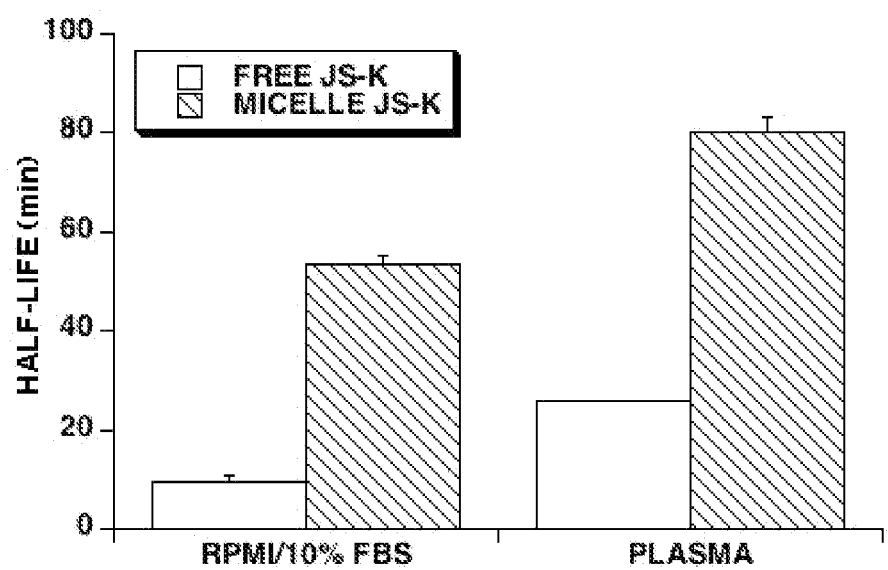
FIG. 9 shows the half life of free JS-K and JS-K incorporated into Pluronic® P123 and exposed to GSH, serum, and RPMI/10% FBS.

The stability of JS-K in different media in vitro was evaluated. JS-K was loaded in Pluronic® P123 micelles at a ratio of JS-K to P123 of 2.25%. Micelle-solubilized JS-K or free JS-K were incubated at 37° C. in the different media at concentrations of 50 and 10 micromolar, respectively. The lower concentrations of free JS-K were used because of its solubility limits. Concentrations of JS-K in the different media were measured at intervals up to 60 minutes using High Pressure Liquid Chromatography (HPLC). Area Under the Curve (AUC) HPLC measurements were used to determine the half-life ($T_{1/2}$) and percent recovery of JS-K in the different media. When added to RPMI media with 10% Fetal Bovine Serum, free JS-K and micelle-solubilized JS-K had a $T_{1/2}$ of 9.6+/−1.3 and 53.4+/−1.96 minutes, respectively (averages and SEM of 6 separate experiments, P=0.00004) (FIG. 9). The percent recovery of free and micelle-solubilized JS-K after a 60 minute incubation in RPMI/10% FBS was 10.53+/−1.42 and 50.71+/−8.27 (averages and SEM of 6 separate experiments, P=0.0001). When added to pooled human plasma, free JS-K and micelle solubilized JS-K had a $T_{1/2}$ of 26+/−0 and 80+/−3 minutes, respectively (averages and SEM of 2 separate experiments, P=0.0353) (FIG. 9). The percent recovery of free and micelle-solubilized JS-K after a 60 minute incubation in pooled human plasma was 39+/−0 and 59.5+/−1.5 (averages and SEM of 2 separate experiments, P=0.05) (FIG. 9).

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A composition produced by the process comprising admixing
   (a) $O^2$-(2,4-dinitrophenyl) 1-[(4-ethoxycarbonyl)piperazin-1-yl]diazen-1-ium-1,2-diolate (JS-K) or the pharmaceutically acceptable salt or ester thereof; and
   (b) a poloxamer having the formula

wherein a is from 50 to 80 and b is from 10 to 25,
   wherein the amount of poloxamer is sufficient to produce a micelle.

2. A pharmaceutical composition comprising the composition of claim 1 and a pharmaceutically acceptable carrier.

3. The composition of claim 1, wherein a is from 50 to 70.

4. The composition of claim 1, wherein the amount of JS-K is less than 0.98% by weight of the micelle.

5. The composition of claim 1, wherein the amount of JS-K is less than 0.52% by weight of the micelle.

* * * * *

UNITED STATES PATENT AND TRADEMARK OFFICE
CERTIFICATE OF CORRECTION

PATENT NO. : 9,005,656 B2  Page 1 of 1
APPLICATION NO. : 12/921227
DATED : April 14, 2015
INVENTOR(S) : Paul J. Shami and Ken M. Kosak It is certified that error appears in the above-identified patent and that said Letters Patent is hereby corrected as shown below:

In the specification

Please replace the paragraph at column 1, lines 15-17 with the following paragraph:

This invention was made with government support under Grant Number CA129611 awarded by the National Institutes of Health. The government has certain rights in the invention.

Signed and Sealed this
Twenty-sixth Day of April, 2016

Michelle K. Lee
*Director of the United States Patent and Trademark Office*